(12) United States Patent
Gibbs et al.

(10) Patent No.: US 6,250,923 B1
(45) Date of Patent: *Jun. 26, 2001

(54) RESORBABLE IMPLANT

(76) Inventors: David Gibbs, 13 Richmond Road, Ottawa, Ontario (CA), K1Y 2X1; Neil Teitelbaum, 834 Colonel By Drive, Ottawa, Ontario (CA), K1S 5C4

( * ) Notice: Subject to any disclaimer, the term of this patent is extended or adjusted under 35 U.S.C. 154(b) by 0 days.

This patent is subject to a terminal disclaimer.

(21) Appl. No.: 09/198,608

(22) Filed: Nov. 24, 1998

Related U.S. Application Data

(63) Continuation-in-part of application No. 08/912,178, filed on Aug. 15, 1997, now Pat. No. 5,888,067.

(51) Int. Cl.$^7$ ........................................ A61C 8/00
(52) U.S. Cl. ........................ 433/173; 433/201.1; 623/16
(58) Field of Search .................... 433/172, 173, 433/174, 175, 176, 201.1; 623/16, 18

(56) References Cited

U.S. PATENT DOCUMENTS

| | | | |
|---|---|---|---|
| 3,707,006 | * 12/1972 | Bokros et al. | 433/201.1 |
| 4,195,366 | * 4/1980 | Jacho et al. | 433/201.1 X |
| 4,673,355 | 6/1987 | Farris et al. | 433/218 |
| 4,976,736 | 12/1990 | White et al. | 623/16 |
| 5,139,424 | * 8/1992 | Yli-Urpo | 433/201.1 X |
| 5,573,401 | 11/1996 | Davidson et al. | 433/201.1 |
| 5,632,927 | 5/1997 | Ferrier et al. | 252/62.2 |
| 5,639,402 | 6/1997 | Barlow et al. | 264/6 |

FOREIGN PATENT DOCUMENTS 2 010 095   6/1979   (GB) ................ A61C/8/00

* cited by examiner

*Primary Examiner*—Nicholas D. Lucchesi
(74) *Attorney, Agent, or Firm*—Neil Teitelbaum & Associates

(57) ABSTRACT

A dental implant for anchoring in bone, wherein said bone comprises an outer cortical bone section and an inner cancellous bone section is made of a body of resorbable material such as coral, having a portion capable of being wedged into the cancellous bone. The body of coral has a generally cylindrical root portion, an emergent portion capable of being wedged into said outer cortical bone section, and a transgingival coronal portion being sized to extend beyond said emergent portion to end beyond a gingival layer, and an abutment portion and a head for retention of said prosthetic device at the other end, wherein said abutment portion meets said coronal portion at an interface beyond said gingival layer. The body of coral is substantially electroplated with a suitable plating material such as gold. At least some of the root portion is absent said plating material so as to allow the bone to enter the substantially plated body of coral to resorb and replace at least some of the coral.

26 Claims, 3 Drawing Sheets

RESORBABLE IMPLANT

This application is a Continuation-in-Part of application Ser. No. 08/912,178 filed Aug. 15, 1997, now U.S. Pat. No. 5,888,067.

FIELD OF THE INVENTION

This invention relates generally to the field of implants, and more specifically relates to implants that are biocompatible and resorbable by bone.

BACKGROUND OF THE INVENTION

The references listed in this specification, to the extent that they provide exemplary procedural or other details supplementary to those set forth herein, are specifically incorporated herein by reference.

Dental implants used to stabilize dentures or support dental crowns and bridges have been known and have been used fairly extensively in the recent past. Such prior art devices are typically comprised of three components, namely, an implant component for anchoring to the bone, a transgingival component and a separate support component. The support component usually attaches to the transgingival component which, in turn attaches to the anchoring component at about the level of the bone. An artificial tooth or bridge may then be attached to this separate support component. This support component is sometimes referred to as an abutment portion, the transgingival component is sometimes referred to as an abutment connection or the transgingival collar or the transepithelial connection and the implant is sometimes referred to as a fixture. An example of such a prior device is found in Canadian Patent No. 1,313,597. This patent describes an implant for insertion into bone through an epithelial and fibrous connective tissue layer to which a prosthesis may be attached. This implant comprises a top portion for supporting a mechanical component to which the prosthesis may be connected and a body comprising an upper bone attachment region, which tapers to a lower bone engagement region having a porous surface. The upper bone attachment region comprises a substantially non-porous but bioreactive surface and this patent teaches that this results in an upper bone attachment region which is claimed to be capable of enhancing bone attachment.

However, several problems develop with an implant of this type. In particular, the patent teaches use of a collar 14 that is adapted to be coupled to the implant 12. However the interface between the collar 14 and the implant 12 occurs at a level below the gingiva in the installed position. Further, although the patent teaches providing recesses 40 on the lower surface 42 of the collar 14 to compliment projections 32 of the implant 12 to prevent rotation between the two components, in practice this is not effective. The attachment between the collar and the implant is accomplished by means of a threaded screw identified as 46 in FIG. 1. Such a screw has a natural tendency to become loose during the vigorous stresses to which an implant of this type is subjected.

To avoid problems associated with the loosening of the threaded screw 46, practitioners have resorted to insertion of cement into the threaded portion to ensure a locked and non-loosening joint between the implant component and the support component.

However, a basic problem with this structure and method still remains. Substantial forces are exerted upon a very small region where the screw is affixed within the jaw. These forces are focused about a small region about point rather than being distributed. Using a plurality of closely set screws disadvantageously lessens the amount of material to which the implant may be affixed.

Unfortunately, screws eventually become loose, and damage to the bone into which they are affixed is permanent. Thus repeated re-tightening or insertion of new screws is limited and not practicable.

It is an object of this invention to provide a "snowshoe-like" effect wherein an implant is securely affixed becoming joined to bone at a multiplicity of points over a large region.

In the aforementioned prior art implant, unfortunately, because the interface between the collar and the implant is below the gum level, any excess cement will be squeezed out at the interface and may not be noticed by the practitioner since it is hidden from view. Such excess accumulation of cement can create irritation of the gum and the bone and can result in infection and/or implant failure. In addition, all implant systems, (fixture, abutment connection, abutment) which have this type of arrangement have a microgap between the fixture or implant and the abutment connection or the transgingival collar at the level of the bone. This microgap has been called an "sendotoxin generator" by some authorities because it is a region for potential bacterial growth.

Other prior art devices include implants with threaded exteriors, which require extensive and complicated methods for preparation of the gum and bone to accept the insert. As a result, such implants are difficult and expensive to insert and specialists most often do the surgery.

This invention provides an implant and method of fabricating such which obviates difficulties and associated problems with prior art implant systems.

An aspect of this invention relates to the use of a resorbable biocompatible material such as coral, to provide the overall implant structure.

The use of these biocompatible materials is well known to assist in the regeneration of bone defects and injuries. In 1926, DeJong observed the similarities between the powder X-ray diffraction pattern of the in vivo mineral and the hydroxyapatite $(Ca_5B(OH)(PO_4)_3$, (CHA). Calcium compounds, including calcium sulfate (Nielson, 1944), calcium hydroxide (Peltier, 1957), and tricalcium phosphate (TCP) (Albee et al., 1920), have been observed to stimulate new bone growth when implanted or injected into bone cavities (Hulbert et al., 1983). These materials also exhibit good biocompatibility and compositional similarities to human bone and tooth and can serve as resorbable or non-resorbable implants depending on their degree of microporosity.

Some TCP implants are known to be readily resorbable. For example, sintered TCP plugs with pore sizes between 100–200 microns have been implanted in rats (Bhashar et al., 1971). Very rapid bone formation was reportedly observed at three days after implantation, and highly cellular tissue, consisting of osteoblastic and fibroblastic proliferation, was found within the pores. At one week, the size of the implant was reduced, and new bone formation was extensive. After two weeks, connective tissue had infiltrated throughout the ceramic. During the next four weeks, the bony material within the ceramic continued to mature. Electron micrographs indicated that within clast-like cells, ceramic could be depicted in membrane-bound vesicles. The authors concluded that TCP implants were biodegradable, via phagocytosis, the ceramic did not elicit a marked inflammatory response, and connective tissue grew rapidly within the pores. Similar results have also been reported by Cutright et al. (1972) who also implanted TCP in rat tibiae. In this study, the ceramic cavities were filled with osteoid and bone after 21 days and the TCP implant was no longer detectable after 48 days.

Larger implants in dogs are reported to elicit slower responses. Cameron et al. (1977) found that TCP implants in dog femurs were completely infiltrated with new bone by four weeks. However, after six weeks, the rate of new bone growth had slowed as the TCP was resorbed. Additionally, only 15% of a 2 cm×2 cm iliac TCP implant in dogs was resorbed after 18 months (Ferraro et al., 1979). Koster et al. (1976) reported the testing of the calcium phosphate formulations monocalcium phosphate, dicalcium phosphate, tricalcium phosphate, tetracalcium phosphate, and combinations consisting of 20% monocalcium phosphate and 80% of either di-, tri- or tetracalcium phosphate as implant materials in dog tibiae. These investigators tested both dense ceramics and porous ceramics with pore sizes between 800–1000 microns. They reported that tissue compatibility is dependent on the $CaO/P_2O_5$ ratio. All materials with ratios between 2/1 and 4/1 are compatible with the optimum ratio being about 3/1 for TOP. After 10 months, Koster et al. (1977) found that tetracalcium phosphate was resorbed only to a minor extent, but that TCP demonstrated lamellar bone growth throughout its pores. Both were found to be tissue compatible. The authors stated that the 3/1 material was not as strong as the 4/1 material and suggested that TCP should be used only in low stress areas while tetracalcium phosphate could be used in high stress environments. Jarcho et al. (1976, 1977) reported the development of a process for preparing dense, polycrystalline, calcium hydroxyapatite (CHA), with the empirical formula 2 $(Ca_5(PO_4)_3OH)$ or $(3Ca_3(PO_4)_2)Ca(OH)_2$. In this study, plugs were fabricated at 100% density and implanted in dogs. No evidence of tissue inflammation occurred, and in contrast to the porous TCP implants described above, little resorption or biodegradation was observed after six months. Holmes (1979) reported that resorption did occur in porous CHA structures. These results led deGroot (1980) to suggest that all calcium phosphates are degradable (resorbable), but the rate is determined by the degree of microporosity. A dense calcium phosphate with negligible porosity would thus degrade only nominally. These results seem to be verified by Farris et al. (U.S. Pat. No. 4,673,355), who claim biocompatible materials with good properties over the range of Ca/P atomic, or molar, ratios from 0.1 to 1.34. These ratios convert to $CaO/P_2O_5$ ratios between 0.2 and 2.68, lower than the 3.0 ratio suggested above. They suggest that the Ca/P or $CaO/P_2O_5$ ratio is not critical for implant applications. Ca/P ratios in the range 0.1 to 2.0 probably show satisfactory biocompatibility. Capano (1987) found that a Ca/P ratio of 0.5, which corresponds to calcium metaphosphate ("CMP"), has the best biocompatibility when implanted in small animals. As the apatites are nearly identical in properties and chemical compositions to bone and tooth enamel, a considerable amount of synthetic effort has been done in this area. Patents in this area include: U.S. Pat. Nos. 4,046,858; 4,274,879; 4,330,514; 4,324,772; 4,048,300; 4,097,935; 4,207,306; and U.S. Pat. No. 3,379,541. All of these patents are incorporated herein by references. Several patents describe methods for treating apatite materials to render implantable shapes. These methods of heating and compaction under pressure in molds produce solid porous articles in various shapes. These patents include: U.S. Pat. Nos. 4,673,355; 4,308,064; 4,113,500; 4,222,128; 4,135,935; 4,149,893; and U.S. Pat. No. 3,913,229. Several patents speak to the use of laser radiation to bond apatite materials to tooth and other surfaces, for example, U.S. Pat. No. 4,673,355 and U.S. Pat. No. 4,224,072. Other patents describe the use of particulate or compacted apatite in conjunction with various compounds, filler, and cements, for example, U.S. Pat. Nos. 4,673,355; 4,230,455; 4,223,412; and U.S. Pat. No. 4,131,597. The aforementioned patents are all incorporated herein by reference. The above discussion indicates that calcium phosphates or compounds, such as CHA that are substantially TCP (Monsanto, for example, markets CHA as TCP), are useful for a variety of bioceramic applications because they are biocompatible and can be fabricated into shapes that have a desirable combination of strength, porosity, and longevity for particular sorbable and non-sorbable needs. Virtually any calcium and phosphate source can be used to prepare materials of interest.

This is explained in more detail in U.S. Pat. No. 5,639,402 issued Jun. 17, 1997 and entitled Method for fabricating artificial bone implant green parts, incorporated herein by reference.

Some more recent advances are the development of hydroxyapatite (CHA) and calcium phosphate powders that can be processed to yield porous resorbable bone facsimiles (U.S. Pat. No. 4,673,355); the development of the SLS.TM. process for directly shaping complex porous structures from thermally fusible polymer/ceramic powders without molds (U.S. Pat. No. 5,076,869); the development of low temperature infiltration and cementing techniques to prepare and replace the polymer binder with ceramic binder (U.S. Pat. No. 5,284,695); and the development of techniques for converting computed tomographic ("CT") information into three-dimensional mathematical files that can automatically guide the SLS.TM. process (Levy et al., 1992; Levy et al., 1994).

More recent work has been directed at expanding the utility of the SLS.TM. apparatus by preparing polymer-coated ceramic powders from spray dried mixtures of water, inorganic particulate, and a custom-synthesized, emulsified, nanometer-sized, polymer binder (Barlow, 1992; Vail et al., 1992). Ceramic composites made by this approach are relatively large, 10–50 microns, agglomerates of polymer-coated inorganic particles. These agglomerate powders may spread easily into uniform layers and fuse readily in the SLS.TM. machine to yield porous "green" parts that have relative densities near 50%, excellent connected internal porosity, and sufficient strengths to be easily handled and shipped. Interconnected pores in bioceramics are often difficult to achieve and are very important in fostering bone growth and for preparing metal matrix/ceramic parts, artificial hips. Polymethyl methacrylate (PMMA) has also been used to form green composites with alumina and with silica/zircon (U.S. Pat. No. 5,284,695). In this process, an appropriate ceramic silicate colloid is used to infiltrate the connected pores of the polymer-bound green part, the colloid is solidified below the fusion temperature of the binder to maintain part geometry, the binder is then thermally removed and the part fired at typically 1000.degree. C. to form porous, all ceramic parts that are suitable for use as cores and molds for metal castings. Such parts typically have only a 1% linear shrinkage, relative to the green state. Their strengths and porosities can be adjusted by additional infiltration and firing treatments. Lagow and co-workers have recently described the chemical synthesis of high strength CHA (U.S. Pat. No. 4,673,355) and long-chain calcium polyphosphate bioceramic powders ("CPB") (Capano, 1987; Nelson et al., 1993). CPB powder is a pure calcium phosphate material with condensed phosphate chains (as shown below) with degrees of polymerization often greater than 120. These materials produce sintered materials that have compressive strengths greater than 200,000 psi and flexural strengths in excess of 20,000 psi. These strengths are about twice that of porcelain used to make dental crowns. Using the Lagow CHA material, Lagow and Friedman have recently completed the first successful, year duration, mandible implant in a canine. Work with CPB implants has demonstrated by electron microscopy backscattering that new bone growth occupied nearly 55% of the volume of a CPB implant in the alveolar (tooth bearing) ridge of a dog, after only four months (Nelson et al., 1993).

It is an object of this invention to provide a dental implant that overcomes many of the disadvantages of known implants.

It is an object of this invention to provide an implant that will be substantially resorbed and replaced with bone.

SUMMARY OF THE INVENTION

In accordance with the invention, there is provided, an implant for securing to bone, comprising:
a body of resorbable material having a root portion for mating with the bone and a second portion adjacent thereto covered with a suitable structural material so as to substantially provide a structural outer shell covering a substantial portion of the resorbable material above the root portion, wherein at least some of the root portion is sufficiently exposed so as to allow the bone to resorb and replace at least some of the resorbable material within the outer shell.

In accordance with the invention, there is further provided, a dental implant for anchoring in bone, comprising:
a body of resorbable material being sized to be contained within and below an upper surface of a trough provided in an alveolar ridge, said body having a root and second portion, the root portion for connecting with the bone at the base of the trough and the second portion adjacent thereto being covered with a suitable protective structural material so as to substantially protect the resorbable material above the root portion, at least some of the root portion being exposed so as to allow the bone to enter the second portion of the resorbable material to resorb and replace at least a portion of the resorbable material.

In accordance with another aspect of the invention, there is provided, a method of providing an implant in bone comprising the steps of:
providing a body of resorbable material having a root portion for mating with the bone and a second portion adjacent thereto covered with a suitable structural material so as to substantially provide a structural outer shell covering a substantial portion of the resorbable material above the root portion, wherein at least some of the root portion is sufficiently exposed so as to allow the bone to resorb and replace at least some of the resorbable material within the outer shell;
exposing a portion of the bone by removing tissue covering the bone;
providing a trough within the exposed portion of the bone, the trough being sized to receive the implant;
placing the root portion of the implant into the trough such that the root portion is disposed adjacent the trough;
and containing the implant within the trough in such a manner as to prevent it from being removed from within the trough for a duration of time, sufficient for at least some of the bone within the trough to resorb at least some of the resorbable material.

BRIEF DESCRIPTION OF THE DRAWINGS

Exemplary embodiments of the invention will now be described in accordance with the drawings in which.

DETAILED DESCRIPTION

Figure 1:
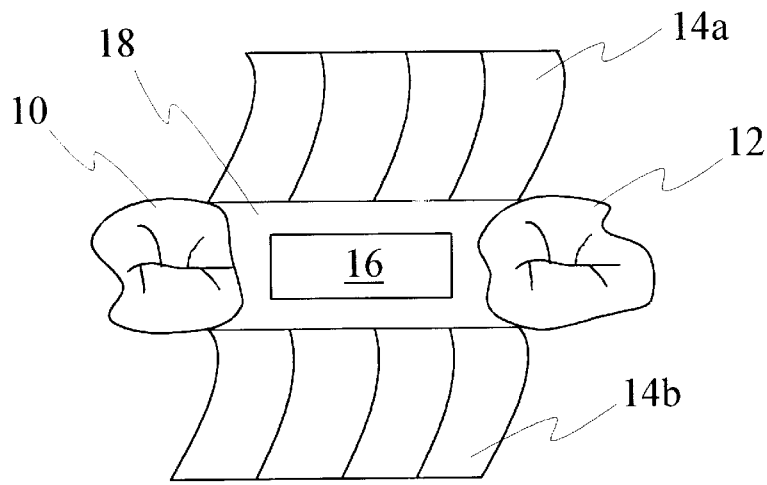
FIG. 1 is a diagrammatic view of an exposed bone region after surgically exposing a region between two spaced teeth.

Turning now to the figures, and more particularly FIG. 1, two teeth 10 and 12 are shown having a spaced region therebetween wherein a tooth had previously been extracted. Surgically flaps 14a and 14b of tissue are shown which expose the tissue 18 and bone 16 below in a conventional manner prior to wedging an implant into a trough 50 in the inner cancellous bone region 16.

The implant in accordance with this invention is preferably made of a bio-resorbable material such as coral or hydroxyapetite that has been substantially coated with a structural material, for example a metallic material such as silver, gold or titanium. However, it is essential to provide a region or a plurality of sub-regions of the coral absent of plating material, to allow bone, adjacent thereto to make contact with and digest the coral.

Conveniently, the coral can be coated with the metallic material by way of electroplating. When the coral becomes coated with the plating material, the metallic material penetrates the pores within the coral and becomes well anchored. The structural material must be able to provide structure to the resorbable material and bone that later resorbs said material and the structural material covering or coating the resorbable implant should be able to withstand forces normally associated with mastication. Such materials comprise gold, silver, titanium and other metals. Alternatively, a non-metallic material such as a ceramic material can be used. In this instance a small ceramic cup-like structure can be filled with a bioresorbable material such as hydroxyapatite forming the covered bioresorbable implant. However, conveniently electroplating the implant will provide a suitable structural coating which adheres and binds well to coral.

Electroplating is well known and relates to the coating of an object with a thin layer of some metal through electrolytic deposition. The process is widely used, for the purpose of rendering a lustrous non-corrosive finish on some article. In electroplating the general object is to employ the article to be plated as the cathode in an electrolytic bath composed of a solution of salt of the metal being plated. The other terminal, the anode may be made of the same metal, or it may be some chemically unaffected conductor. A low-voltage current is passed through the solution, which electrolyzes and plates the cathodic articles with the metal to the desired thickness.

A variety of methods are described for electroplating of non-conductive materials; for example, U.S. Pat. No. 5,632,927 in the name of Ferrier, et. al. issued May 27, 1997, entitled Process For Preparing A Non-Conductive Substrate For Electroplating discloses the modification of carbon particles for achieving enhanced plating upon a non-conductive surface which has been previously treated with the modified carbon particles.

U.S. Pat. No. 5,597,471 in the name of Ragge, et. al. issued Jan. 28, 1997 entitled Solution For Coating Non-Conductors With Conductive Polymers and their Metallization Process discloses a process for metallizing non-conductive surfaces, by treating the non-conductive surface with a solution containing at least one suspended or solute oxidation agent, contacting the treated non-conductive surface with an acidic solution containing at least one water soluble polymer selected from the group consisting of homopolymers and copolymers, and at least one aromatic compound which chemically polymerizes the water-soluble polymer and the aromatic compound to form a conductive polymer, and electroplating the conductive polymer. Each water-soluble polymer contains uncharged structural elements or is cationic polyelectrolyte. Additionally, each water soluble polymer is capable of protonizing/deprotonizing reactions, formation of hydrogen bridge compounds and van der Waals interactions.

Other United States patents that relate to electroplating non-conductive materials are: U.S. Pat. Nos. 4,374,709, 5,492,613, and 5,589,270 all incorporated herein by reference.

FIGS. 2a to 2d illustrate the implant at various stages of manufacture in accordance with a first embodiment. A bio-resorbable material in the form of a coral block 20 is first provided as the base material for the implant. The coral block 20 is sized and shaped in such a manner as to be suitable for fitting within the trough 50 defined in the exposed bone 16 between teeth 10 and 12. In a preferred embodiment shown in FIG. 2b, the coral 20 is shaped in such a manner as to have at an upper end, an abutment 22 for cementing to a complementary under surface of a crown (not shown). This embodiment obviates the requirement for screws or similar attachments. Alternatively, as is shown in FIGS. 4 to 7, a recess 54 is formed in the upper surface of the implant. More particularly in FIGS. 5 to 7 the recess is sized to accommodate a temporary post 60 preferably made of a strong plastic or polymer that can later be removed with sufficient force after the implant has been resorbed by the bone 16 it is coupled therewith.

Figure 2A:
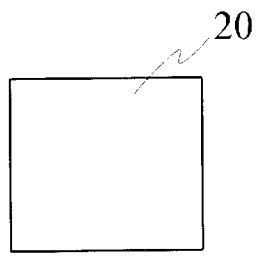
FIGS. 2a to 2d illustrate the implant at various stages in production.
Figure 2B:
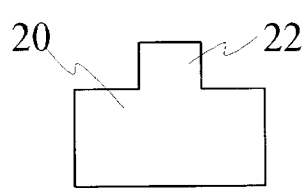
Figure 2C:
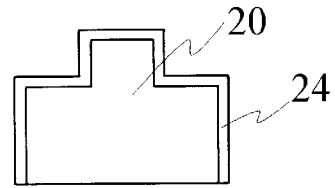

FIG. 2c illustrates the coral implant 20 after having been coated via a plating process wherein a substantial portion of the implant is plated with gold or other suitable metallic material 24. As is shown, the bottom portion of the implant is unplated as it is coated with a plating resistive material such as wax, prior to electroplating. The purpose of not plating a portion of the coral, or removing a portion of the plating on the coral is that the coral material must be in direct contact with the bone 16 for digestion/resorbing of the coral by the bone 16 to take place.

Alternatively, the entire coral implant may be coated by electroplating, and later, the bottom portion ground to remove the coral coating deposited thereon.

In another embodiment not shown, a bioresorbable implant is coated and substantially encapsulated by a metallic container by packing resorbable material within the metallic container in a soft or semi-liquid state and allowing the resorbable material to harden.

Preferably, the inner walls of the container are roughened or coated with micro-springs of titanium to assist in the bonding between bioresorbable material and the container substantially encapsulating it. Of course it is necessary to have at a portion, and preferably all of the root portion of the implant exposed so that the bone it is to be implanted in can resorb the material within the container.

Figure 2D:
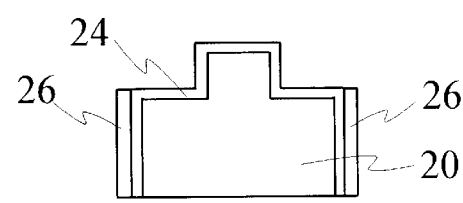

FIG. 2d shows the implant after having undergone a preferred but not required step. After the implant is electroplated, the gold coating is then used as a substrate for depositing thereon a layer of titanium 26, through a process such as vapour deposition. This titanium layer enhances the interface attachment between the gum tissue adjacent the bone 16, and the implant.

The benefits of using titanium are well known and described in U.S. Pat. No. 5,573,401 in the name of Davidson, et. al., issued Nov. 12, 1996 entitled Biocompatible, low modulus dental devices discloses dental devices (including implants, abutments, bridges, screws, and orthodontic appliances) that are fabricated from low modulus, biocompatible, non-toxic Ti—Nb—Zr alloys. The dental implants provide a biomaterial-to-bone interface that results in significant attachment between implant and bone. The implants may be supplied with a porous coating or macro-texture to promote bone attachment and stabilization of the implant in the jawbone.

Figure 3:
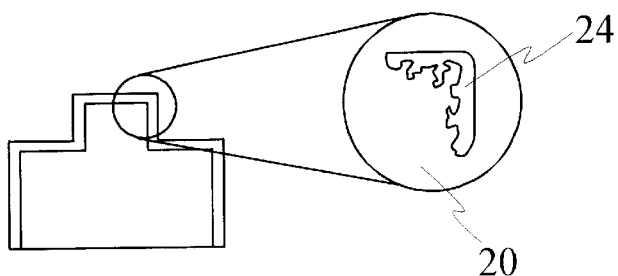
FIG. 3 is a cross-sectional partial view of the electroplated resorbable implant; and, FIG. 4 is a cross sectional view of an alternative embodiment wherein a post is affixed to the resorbable implant prior to electroplating.

Referring now to FIG. 3, a partial cross-section of an implant in accordance with the invention is shown (not to scale); the adjacent gold-coated and coral regions in the illustration are shown magnified to illustrate the nature of the bond therebetween. Since the coral is a semi-porous substance, the gold plating enters the pores within the coral and essentially forms hook-like attachments within the coral substrate.

After the implant is surgically placed into the bone 16, the coral is digested /resorbed by the bone 16. Once the resorption is essentially complete, and the coral is replaced by bone the implant is immovable. Obviously, the aforementioned problems and difficulties associated with prior art implants attached by screws are obviated by this invention.

Numerous other embodiments may be envisaged without departing from the scope of the invention.

Figure 4:
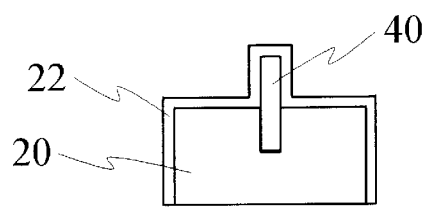

For example, instead of shaping the upper portion of the coral to have an abutment for attaching to a crown, a metal screw or post 40 can be affixed into the coral, prior to electroplating. After electroplating the coral and protruding screw head or post, the plated screw head or post being integral with the coral provides a surface for affixing to the undersurface of the crown. This is shown in FIG. 4. Once the screw/post is electroplated and integrated as a monolithic structure, the "snowshoe-like" effect is achieved once the device is implanted.

In another embodiment, instead of implanting for dental purposes, a plated biocompatible implant as described according to the invention is implanted in bone matter other than the jaw for attaching to a prosthetic device or the like. The use of the plating distributes force exerted upon a prosthetic device more evenly across new bone material and therefore is advantageous.

In yet another embodiment, implanting a plated bioresorbable material upon joints to resurface abraded or pitted joints can be realized in a similar manner. For example, a femur/hip joint can be resurfaced using a plated bioresorbable implant in accordance with this invention wherein, for example the femoral head may have a portion of its outer surface that is partially or is totally resurfaced with an implant that conforms to a complementary receiving surface.

Figure 5:
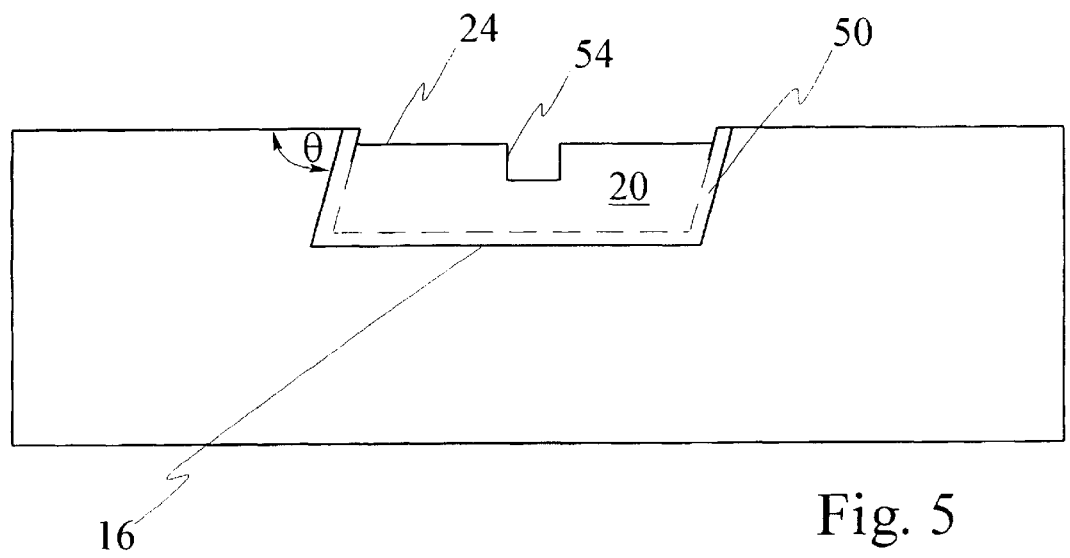
FIG. 5 is a cross sectional view of an alternative embodiment of the invention in situ in the alveolar ridge, wherein a recess is provided in an upper surface of the resorbable implant.

Referring now to FIG. 5 it should be noted that the cavity or trough 50 includes walls that are slanted so as to receive an implant having complementary slanted walls. Here the angle is shown to be less than 90 degrees. The provision of slanted wall assists in the adhesion of the implant within the trough 50 by providing some form of locking and resistance of upward movement.

Figure 6:
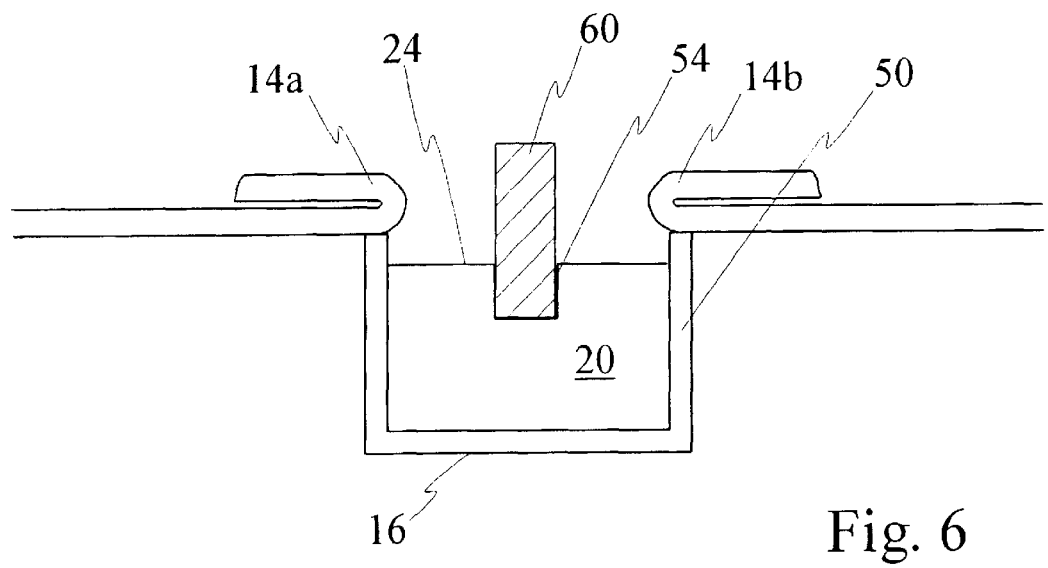
FIG. 6 is a cross sectional side view of the implant in accordance with the invention in situ in the alveolar ridge, the implant having a temporary post within the recess.
Figure 7:
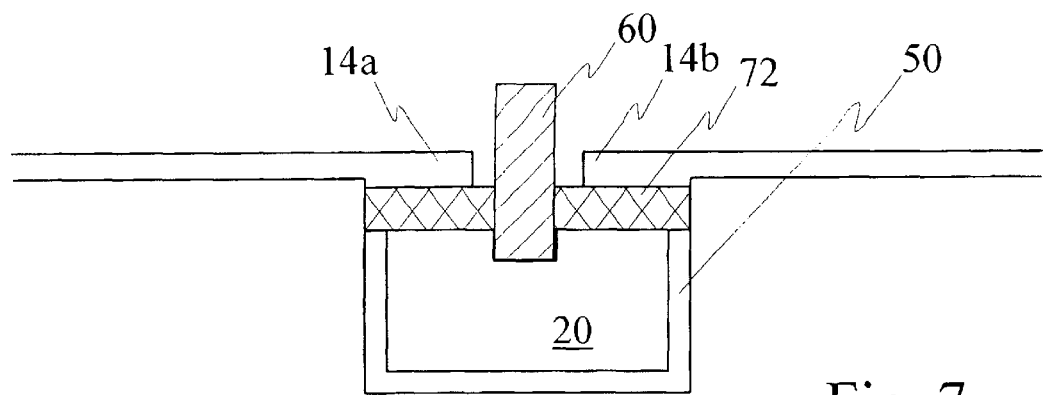
FIG. 7 is a cross sectional side view of the implant in accordance with the invention in situ in the alveolar ridge as shown in FIG. 6 and having a bioresorbable packing material placed over the implant to induce bone growth over the upper surface and about the sides of the implant.
Figure 8:
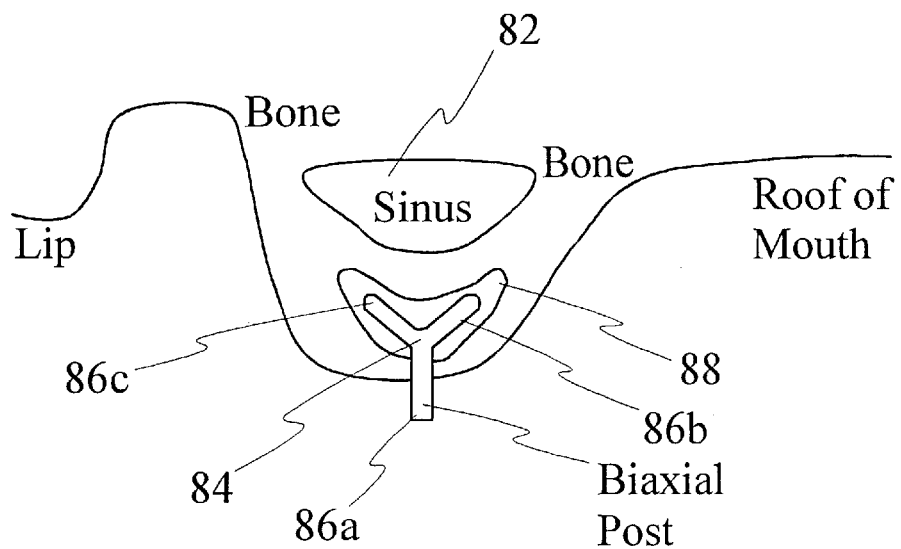
FIG. 8 is a top view of an implant shaped and sized to fit around a sinus cavity within the alveolar ridge.
Figure 9:
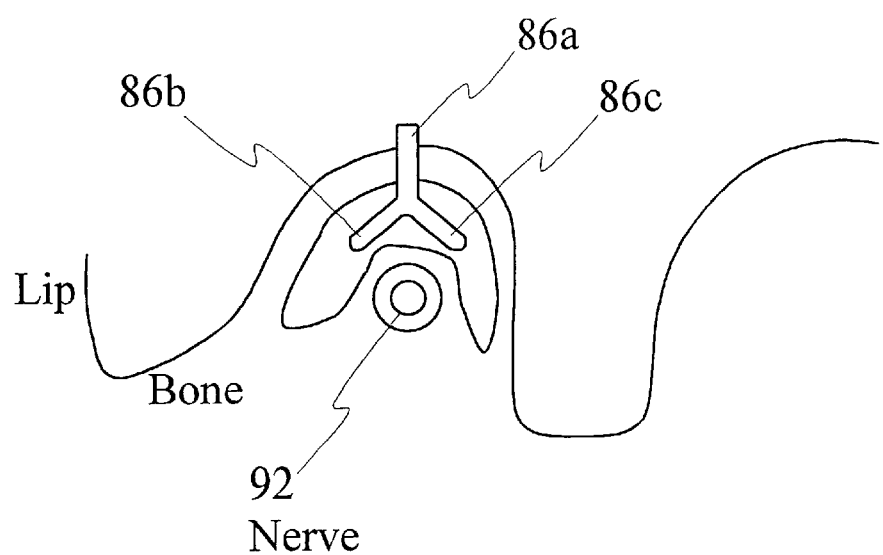
FIG. 9 is a top view of an implant shaped to fit around a nerve.

Turning now to FIG. 6, an implant 20 has disposed therein, a temporary post 60 held within the recess 54 of the plated bioresorbable block. In FIG. 7 a bioresorbable packing material is placed over the implant and around the post 60 to promote bone growth around and about the top and upper sides of the implant 20. Subsequently, the surgical flaps 14*a* and 14*b* of tissue are replaced and sutured according to conventional practice. After the implant has become sufficiently anchored, in approximately 6–8 weeks, the temporary post 60 is removed, the flaps 14*a* and 14*b* are once again opened and a crown having a complementary post conforming to the recess 54 is cemented to the implant.

What is claimed is:

1. An implant for securing to bone, comprising:
a body of resorbable material having a root portion for mating with the bone and a second portion adjacent thereto coated with a suitable structural material which substantially provides a structural outer shell coating a substantial portion of the resorbable material above the root portion, wherein at least some of the root portion is sufficiently exposed so as to allow the bone to resorb and replace at least some of the resorbable material within the outer shell.

2. An implant as defined in claim 1 wherein the resorbable material is comprised of coral.

3. An implant as defined in claim 1, wherein the resorbable material is comprised of hydroxyapatite.

4. An implant as defined in claim 1, wherein the suitable structural material is comprised of metal.

5. An implant as defined in claim 4, wherein the metal is coated on the resorbable material.

6. An implant as defined in claim 5, wherein the metal is plated on the resorbable material.

7. An implant as defined in claim 5, wherein the resorbable material has pores therein sized to accept and bond with the metal structural material.

8. An implant as defined in claim 7, wherein the resorbable material is coral.

9. An implant as defined in claim 1, wherein the implant is for supporting a crown.

10. A implant as defined in claim 9, wherein the implant is a dental implant having an upper surface having a recess therein for receiving a complementary post.

11. A dental implant as defined in claim 10 wherein the upper surface of the implant is coated with a metal.

12. A method of providing an implant in bone comprising the steps of:
providing a body of resorbable material having a root portion for mating with the bone and a second portion adjacent thereto coated with a suitable structural material which substantially provides a structural outer shell coating a substantial portion of the resorbable material above the root portion, wherein at least some of the root portion is sufficiently exposed so as to allow the bone to resorb and replace at least some of the resorbable material within the outer shell;
exposing a portion of the bone by removing tissue covering the bone;
providing a trough within the exposed portion of the bone, the trough being sized to receive the implant;
placing the root portion of the implant into the trough; and,
containing the implant within the trough in such a manner as to prevent it from being removed from within the trough for a duration of time, sufficient for at least some of the bone within the trough to resorb at least some of the resorbable material.

13. A method of providing an implant in bone as defined in claim 12, further comprising the step of providing a resorbable filling material over the implant before containing the implant within the trough by covering the implant with tissue.

14. A dental implant for anchoring in bone, comprising:
a body of resorbable material having a root and second portion, the root portion for connecting with the bone and the second portion adjacent thereto being covered with a suitable protective structural material so as to substantially protect the resorbable material above the root portion, at least some of the root portion being exposed so as to allow the bone to enter the second portion of the resorbable material to resorb and replace at least most of the resorbable material.

15. A dental implant as defined in claim 14, wherein the suitable protective structural material is comprised of metal.

16. A dental implant as defined in claim 15 wherein the metal is coated on the resorbable material.

17. A dental implant as defined in claim 15, wherein the metal is plated on the resorbable material.

18. A dental implant as defined in claim 14, wherein an upper surface of the second portion includes a recess for receiving a post.

19. A dental implant as defined in claim 18, comprising a post temporarily held within the recess.

20. A dental implant as defined in claim 18, comprising a crown, having a post for mating with the recess within the upper surface of the second portion.

21. A dental implant as defined in claim 14, sized to fit within a trough provided within the alveolar ridge.

22. A dental implant as defined in claim 21, wherein the implant is sized to be below the an upper surface of the alveolar ridge when placed within the trough so as not to protrude above the alveolar ridge.

23. A dental implant as defined in claim 14, wherein the second portion of the body of resorbable material is at least substantially contained within a container having inside and outside walls, the container formed of the suitable protective structural material.

24. A dental implant for anchoring in bone, comprising:
a body of resorbable material being sized to be contained within and below an upper surface of a trough provided in an alveolar ridge, said body having a root and second portion, the root portion for connecting with the bone at the base of the trough and the second portion adjacent thereto being covered with a suitable protective structural material so as to substantially protect the resorbable material above the root portion, at least some of the root portion being exposed so as to allow the bone to enter the second portion of the resorbable material to resorb and replace at least a portion of the resorbable material.

25. A dental implant for anchoring in bone, wherein said bone comprises an outer cortical bone section and an inner cancellous bone section, said implant comprising:

a body of coral, having a portion capable of being wedged into the cancellous bone section, the body of coral having a generally cylindrical root portion, an emergent portion capable of being wedged into said outer cortical bone section, and a transgingival coronal portion being sized to extend beyond said emergent portion to end beyond a gingival layer, and an abutment portion and a head for retention of said prosthetic device at another other end, wherein said abutment portion meets said coronal portion at an interface beyond said gingival layer, the body of coral being substantially electroplated with a suitable plating material; at least some of the root portion being absent said plating material so as to allow the bone to enter the substantially plated body of coral to resorb and replace at least some of the coral.

26. A dental implant for anchoring in bone, comprising:

a body of resorbable material, having a root portion capable of being coupled with the bone and an upper portion adjacent the root portion the upper portion of the resorbable material being substantially coated with a suitable metallic material so as to substantially encapsulate the resorbable material above the root portion; at least some of the root portion being absent said metallic material so as to allow the bone to enter the body of the resorbable material to resorb and replace at least most of the resorbable material.

* * * * *